United States Patent [19]

Jones

[11] Patent Number: 4,922,962

[45] Date of Patent: May 8, 1990

[54] PNEUMATIC OSCILLATORS

[75] Inventor: Norman S. Jones, Stanbridge, England

[73] Assignee: Instruments and Movements Limited, London, England

[21] Appl. No.: 352,966

[22] Filed: May 17, 1989

[30] Foreign Application Priority Data

May 20, 1988 [GB] United Kingdom ............... 8812007

[51] Int. Cl.$^5$ ............................................. F16K 31/36
[52] U.S. Cl. ............................... 137/624.14; 251/900; 137/904
[58] Field of Search ............. 137/624.14, 904, 624.13, 137/624.15; 251/900

[56] References Cited

U.S. PATENT DOCUMENTS

| | | | |
|---|---|---|---|
| 2,092,819 | 9/1937 | Tennant | 137/904 X |
| 2,141,847 | 12/1938 | Tennant | 137/904 X |
| 3,216,328 | 11/1965 | Peterson | 137/624.14 X |
| 3,881,480 | 5/1975 | Lafourcade | |
| 4,234,162 | 11/1980 | Kay | 251/900 X |
| 4,418,924 | 12/1983 | Mack | 251/900 X |

FOREIGN PATENT DOCUMENTS 1530478  6/1968  France .
1533550 11/1978  United Kingdom .

Primary Examiner—Alan Cohan
Attorney, Agent, or Firm—Arnold B. Silverman; David V. Radack

[57] ABSTRACT

A pneumatic oscillator of the type having an operating piston reciprocable in a cylinder to control a poppet valve arrangement so as to control a gas flow path, and biassed to the flow path-closing condition with feedback of output supplementary to the bias in opposition to source pressure, is characterized by a piston seal comprising an O-ring having both radial and axial clearance in a retaining groove in the piston to provide low friction, and by a resilient buffer to arrest the piston at its stroke-end in the flow path-opening position and to cause piston rebound to an extent to position the O-ring against the lateral groove wall that is downstream to the prevailing pressure differential, thereby to ensure effective sealing at the switching point. The buffer also suppresses noise of operation of the oscillator. The oscillator is particularly useful for generating breathable gas pulses for resuscitation and/or lung ventilation purposes.

3 Claims, 1 Drawing Sheet

PNEUMATIC OSCILLATORS

BACKGROUND OF THE INVENTION

1. Field of the Invention

This invention concerns pneumatic oscillators, especially but not exclusively for the operation of resuscitators and/or ventilators and like devices for inducing or assisting lung function in human patients.

2. Background Discussion

In general, such devices generate a train of pulses of breathable gas that is ducted to a patient, usually via a so-called patient valve and/or an oronasal mask or tracheal intubation device. The generation of the pulse train with pulses at the required intervals and with appropriate tidal flow characteristics requires some form of switching mechanism controlling the flow of breathable gas from a source to the pulse output. Simplicity, reliability and constancy of performance in service, and robustness are dominant criteria in the design of resuscitators or ventilators, especially those intended for use by emergency services such as ambulance crews, or for use in a domestic environment by non-specialist operators.

The Prior Art

Pneumatic oscillators exist in various forms and many forms have been applied to this purpose. GB-A-1 533 550 exemplifies one such form of pneumatic oscillator that has been successfully applied in practice but even that oscillator comprises several components and several moving parts, with consequent complexity and cost.

In another form of pneumatic oscillator, a piston or its equivalent is reciprocable to open and close a flow path between a source of pressurized breathable gas and a pulse output. The piston is biassed towards the flow path-closing position and the biassing is supplemented by gas pressure derived from the output of the device. Source gas pressure is applied to the piston in a manner to overcome the biassing so as to cause the piston to move to its flow path-opening position; whereupon the device outputs a gas pressure pulse from which pressure is derived to supplement the biassing and restore the piston to its flow path-closing position. Examples of such an oscillator are disclosed in FR-A-1 530 478 and US-A-3 881 480.

To obtain a snap-action in the opening and closing of the flow path, a poppet valve arrangement is utilised in which a sealing lip coacts, in the flow path-closing condition, with a resilient facing in such a manner as to isolate an area of the piston or equivalent from the gas pressure acting elsewhere. Accordingly, when the flow path is open, gas pressure is applied to a different area than when the flow path is closed with the consequence that there is an abrupt change of effective area exposed to gas pressure at the point of switching, and an abrupt change in the force balance on the piston.

Although an oscillator of this general form exhibits remarkable simplicity and would appear to be eminently suitable for the applications considered, in practice such oscillators have not achieved widespread adoption because the attainment of accurate and reproducible performance characteristics depends critically upon the maintenance of close tolerances in manufacture and even then the characteristics tend to change, unpredictably, in service. The reason for this is that the characteristics are critically affected by the force balance on the piston or its equivalent at the point of switching and this in turn is influenced by a number of factors. One such factor is the effectiveness of the seals exposed to gas pressure at the point of switching, and the friction forces due to these seals.

Piston sealing may conveniently be accomplished by the use of one or more O-rings. However, if an O-ring is accommodated in a retaining groove of such dimensions that it is compressed radially, high and often variable friction forces arise. On the other hand, if an O-ring is accommodated in a retaining groove dimensioned to avoid radial compression and so avoid the generation of high friction forces, the O-ring must normally be allowed some axial clearance in the groove to provide for pressure equalisation, with sealing of the O-ring against the downstream lateral wall of the groove.

Thus, when an O-ring has axial clearance in its retaining groove and radial clearance from the groove base, it is free to move axially in the groove in response either to the pressure differential across the seal or in response to relative movement between the seal elements—the piston and its cylinder in the case considered. Seal effectiveness is important at all times both during motion of the piston and at its stroke-end positions, and it is therefore important that the O-ring should be appropriately located in its retaining groove to seal against a lateral groove wall, whether the piston is in motion or stationary at the point of switching.

In the pneumatic oscillators of interest, the required bias forces on the piston may be provided by differential action, so that a pair of seals is required, doubling the problem of achieving low friction and effective sealing. However, in preferred forms of the pneumatic oscillator of interest, the bias forces on the piston are provided at least in part by a spring so that the pressure differential across the piston seal is unidirectional. Accordingly, if the piston is sealed by an O-ring having positive axial and radial clearance in a retaining groove in the piston, at one stroke-end position—that in which the poppet valve arrangement is in a flow path-closing condition—the O-ring will be appropriately located in its retaining groove, whereas at the other stroke-end position the O-ring tends to come to rest in an inappropriate position and some leakage may occur.

SUMMARY OF THE INVENTION

In accordance with the invention, a pneumatic oscillator having an operating piston reciprocable in a cylinder to control a poppet valve arrangement so as to control a gas flow path, and biassed to the flow path-closing condition with feedback of output supplementary to the bias in opposition to source pressure, is characterised by a piston seal comprising an O-ring having both radial and axial clearance in a retaining groove in the piston, and by a resilient buffer to arrest the piston at its stroke-end in the flow path-opening position and to cause piston rebound to an extent to position the O-ring against the lateral groove wall that is downstream to the prevailing pressure differential.

The resilient buffer also assists in reducing the noise of operation of the oscillator.

The preferred resilient buffer is an O-ring disposed to engage the periphery of the adjacent end of the piston.

BRIEF DESCRIPTION OF THE DRAWINGS

The invention is further explained with reference to the accompanying drawings, in which.

DESCRIPTION OF THE PREFERRED EMBODIMENT

Figure 1:
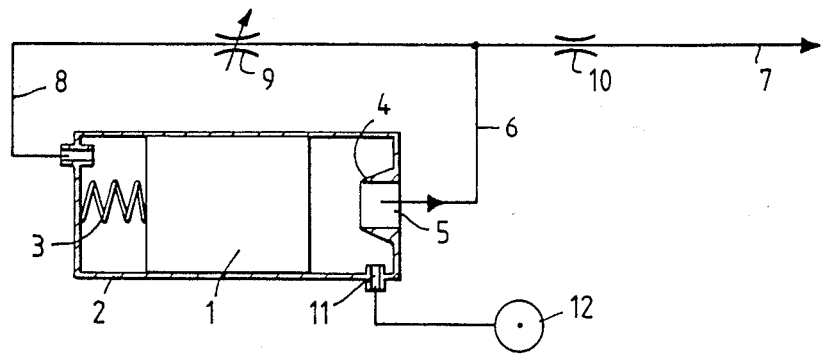
FIG. 1 illustrates diagrammatically the principles of a pneumatic oscillator of the form to which the invention pertains.

The principle of an oscillator of the form to which the invention is applicable is illustrated diagrammatically in FIG. 1 of the drawings. A piston 1 is reciprocable in a cylinder 2 and is biassed by a spring 3 towards the right as seen in the drawing, to engage a sealing lip 4 surrounding a port 5 in the end of the cylinder 2. In the arrangement shown the port 5 constitutes an outlet port connected to an output line 7 by way of an outlet branch 6.

The outlet branch 6 also connects with a feedback line 8 via a restrictor 9, the feedback line 8 connecting with the end of the cylinder opposite to that containing the port 5. A further restrictor 10 is interposed between the outlet branch 6 and the output line 7.

A further port 11 in the end of the cylinder 2 and outboard of the port 5 serves for the admission of pressurized breathable gas, for instance compressed air or oxygen, to this end of the cylinder 2.

The drawing shows the piston 1 in a flow path-opening position clear of the sealing lip 4. In this position of the piston 1, breathable gas can flow from the source indicated at 12 via the ports 11 and 5 to the outlet branch 6 and thence via the restrictor 10 to the output line 7 and also via the restrictor 9 and the feedback line 8 to the left hand end of the cylinder 2 as seen in the drawing. As a consequence of the flow of gas in the branch 6 and the presence of the restrictor 10, gas flows through the feedback line to the left hand end of the cylinder 2 at a rate controlled by the restrictor 9 and builds up pressure therein that acts on the piston 1 to supplement the force of the spring 3. Eventually the combined effects of the gas pressure and spring 3 cause the piston to move to the right as seen in the drawing, towards the sealing lip 4. As the piston approaches the latter, flow to the outlet branch 6 is restricted and the pressure therein drops so that there is a sudden shift in the balance of forces on the piston 1 and this completes its movement to the right with a snap-action, to engage the sealing lip 4 and thus cut off flow to the port 5 and outlet branch 6.

Pressure in the left hand end of the cylinder 2 then decays by reverse flow of gas from the cylinder through the feedback line and restrictors 9 and 10. When the gas pressure in the left hand of the cylinder 2 has decayed to an appropriate extent, the source gas pressure acting on the annular area of the piston 1 outboard of the sealing lip 4, overcomes the force of the spring 3 and causes the piston 1 to commence to move towards the left as seen in the drawing. As it does so, it opens the pathway to the port 5 and gas flows into the outlet branch 6, building up pressure therein which acts on the central area of the piston 1 to supplement the thrust of the source pressure on the outboard annular area of the piston. There is in consequence an abrupt change in the balance of forces acting on the piston 1 which moves with a snap-action to the position shown in the drawing, whereupon the described cycle repeats with a frequency determined by the relationship between the annular area outboard of the sealing lip 4 and the total cylinder area, the bias force supplied by the spring 3 and the characteristics of the restrictors 9 and 10.

The principles of the operation of this form of pneumatic oscillator may be embodied in various arrangements in practical devices. For instance the restrictor 9 may be replaced by various restrictor/non-return valve networks to achieve particular cycling patterns in the output line and to provide different operator control possibilities. The biassing of the piston may be achieved by means other than a spring: for instance the piston may have different areas effective at its opposite ends so that when both ends of the piston are exposed to equivalent pressures it experiences a net thrust towards the flow path-closing position. Whereas in the arrangement shown the port 5 constitutes an outlet port and the port 11 constitutes an inlet, the converse arrangement is possible. Moreover, the sealing lip 4 may be carried by the piston (or its equivalent) to move therewith and coact with a resilient facing on the cylinder end wall, instead of being carried by the latter as in the illustrated arrangement.

Figure 2:
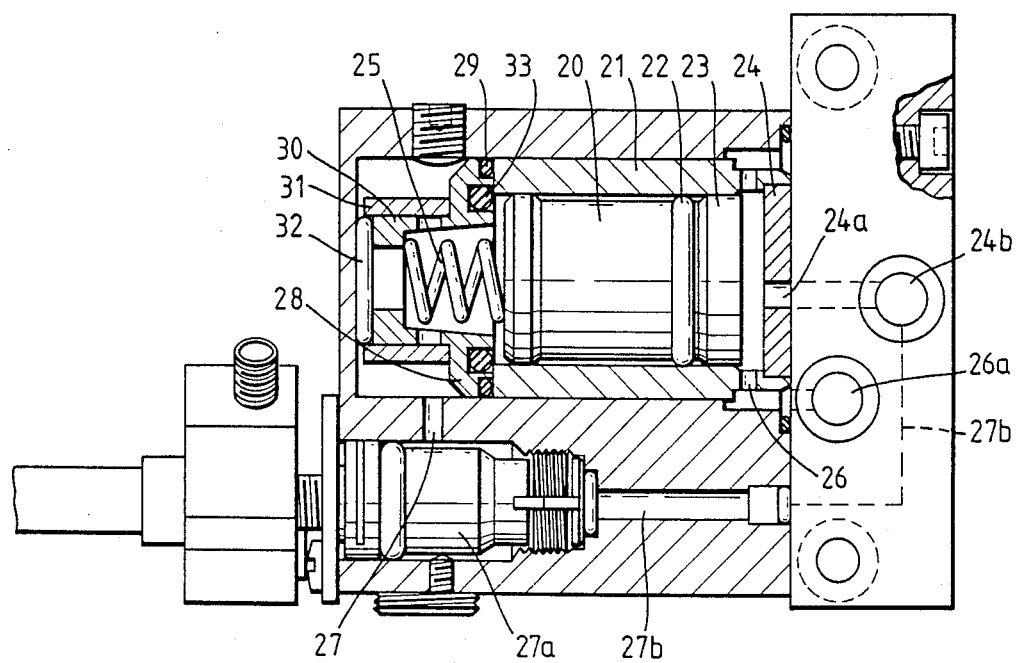
FIG. 2 illustrates an oscillator embodying the invention.

FIG. 2 illustrates a pneumatic oscillator embodying the invention. This oscillator comprises a piston 20 reciprocable in a cylinder defined by a sleeve 21 in a cylinder block and having an O-ring 22 arranged in a retaining groove in the piston, the retaining groove and O-ring being so mutually dimensioned as to provide radial clearance between the O-ring and the base of the groove and a small but positive axial clearance between the O-ring and the groove lateral walls. The O-ring may, for instance, have a section of 1.75 mm and an axial clearance of 0.025 to 0.15 mm.

The right hand end of the piston 20 as seen in the drawing carries a sealing lip (not shown) contained within the end 23 of the piston and that cooperates with a resilient facing 24, outboard of an outlet port 24a, communicating with a terminal 24b, to constitute a poppet valve arrangement. This is preferably of the construction disclosed in copending application Ser. No 352962), herein incorporated by reference. A spring 25 biasses the piston 20 towards the right, the flow path-closing position. A source gas inlet 26 having a terminal 26a, communicates with the right hand end of the cylinder, outboard of the sealing lip on piston end 23, so that source gas pressure is always acting on the outer annular area of the piston and, thus, on the right hand side of the O-ring 22 as seen in the drawing, to tend to urge this into engagement with the left hand lateral groove wall. A feedback connection 27 is provided at the left hand end of the cylinder and communicates with the outlet port 24a via a restrictor assembly 27a and a passage 27b.

The spring 25 is housed in a cap 28 that is sealed against the end of the sleeve 21 by an O-ring 29 and carries the spring in a cup 30 that fits in a porous filter sleeve 31 on the cap 28. An O-ring 32 is trapped between the cup 30 and the end wall of the cylinder.

A resilient buffer in the form of an O-ring 33 is positioned in the cap 28 so as to be engaged by the periphery of the left hand end of the piston 20 when that reaches its left hand stroke-end position, so as to arrest the piston movement and cause it to rebound a small distance to the right, thereby to cause the piston seal O-ring 22 to travel to the left in its retaining groove so as to be ready to seal against the left hand lateral wall of the groove under the influence of the pressure differential (from right to left as seen in the drawing) to which the piston seal is exposed at that time. In this way, leakage at the piston seal is precluded. The buffer action of the O-ring 33 is supplemented by the resilient location of the cup 30 by the O-ring 32 and both O-rings 32 and 33 coact to damp the transmission of noise, engendered by the piston striking the cap 28, to the casing of the valve.

What is claimed is:

1. A pneumatic oscillator having an operating piston reciprocable in a cylinder to control a poppet valve arrangement so as to control a gas flow path, and biassed to the flow path-closing condition with feedback of output supplementary to the bias in opposition to source pressure, characterised by a piston seal comprising an O-ring having both radial and axial clearance in a retaining groove in the piston, and by a resilient buffer to arrest the piston at its stroke-end in the flow path-opening position and to cause piston rebound to an extent to position the O-ring against the lateral groove wall that is downstream to the prevailing pressure differential.

2. A pneumatic oscillator according to claim 1, wherein said resilient buffer comprises a resilient ring positioned to be engaged by the periphery of the adjacent end of the piston.

3. A pneumatic oscillator according to claim 1 or 2, arranged so that source pressure is applied continuously to the piston seal on one side thereof.

* * * * *